United States Patent
Bienstman et al.

(10) Patent No.: US 9,068,950 B2
(45) Date of Patent: Jun. 30, 2015

(54) VERNIER PHOTONIC SENSOR DATA-ANALYSIS

(75) Inventors: Peter Bienstman, Merelbeke (BE); Tom Claes, Ghent (BE); Wim Bogaerts, Melle (BE)

(73) Assignees: UNIVERSITEIT GENT, Ghent (BE); IMEC VZW, Leuven (BE)

( * ) Notice: Subject to any disclaimer, the term of this patent is extended or adjusted under 35 U.S.C. 154(b) by 815 days.

(21) Appl. No.: 13/271,875

(22) Filed: Oct. 12, 2011

(65) Prior Publication Data

US 2013/0094029 A1    Apr. 18, 2013

(51) Int. Cl.
 *G01N 21/41* (2006.01)
 *G01N 21/77* (2006.01)

(52) U.S. Cl.
 CPC ............ *G01N 21/7746* (2013.01); *G01N 21/41* (2013.01)

(58) Field of Classification Search
 None
 See application file for complete search history.

(56) References Cited

U.S. PATENT DOCUMENTS

2012/0298849 A1 * 11/2012 He et al. .................. 250/227.14
2013/0071061 A1 *  3/2013 Tu et al. ......................... 385/12

FOREIGN PATENT DOCUMENTS

WO    WO 2011091735 A1 *  8/2011

OTHER PUBLICATIONS

Daoxin Dai, Highly Sensitive Digital Optical Sensor Based on Cascaded High-Q Ring-Resonators, Optics Express, vol. 17, No. 26, Dec. 21, 2009.
Tom Claes et al., Experimental Characterization of a Silicon Photonic Biosensor Consisting of Two Cascaded Ring Resonators Based on the Vernier-Effect and Introduction of a Curve Fitting Method for an Improved Detection Limit, Optics Express, vol. 18, No. 22, Oct. 25, 2010.
Lei Jin et al., Highly-Sensitive Silicon-On-Insulator Sensor Based on Two Cascaded Micro-Ring Resonators With Vernier Effect, Opt. Commun. (2010), doi: 10.1016/j.optcom.2010.08.035.

\* cited by examiner

*Primary Examiner* — Tina Wong
(74) *Attorney, Agent, or Firm* — Bacon & Thomas, PLLC

(57) ABSTRACT

Quantifying a refractive index of a test medium by obtaining spectral data representative for an optical signal being modulated with an optical transfer characteristics of a photonic sensor, the modulation being obtained by combining modulation of a first electromagnetic wave component in an optical filter element with a first periodic transfer spectrum having a first free spectral range and modulation of a second electromagnetic wave component in an optical filter element with a second periodic transfer spectrum having a second free spectral range being different from the first free spectral range. A relative is change induced in the second periodic transfer spectrum by bringing the test medium in proximity with the optical filter element with the second periodic transfer spectrum. The refractive index of the test medium is quantified by determining a wavelength offset of an envelope signal in said spectral data.

20 Claims, 7 Drawing Sheets

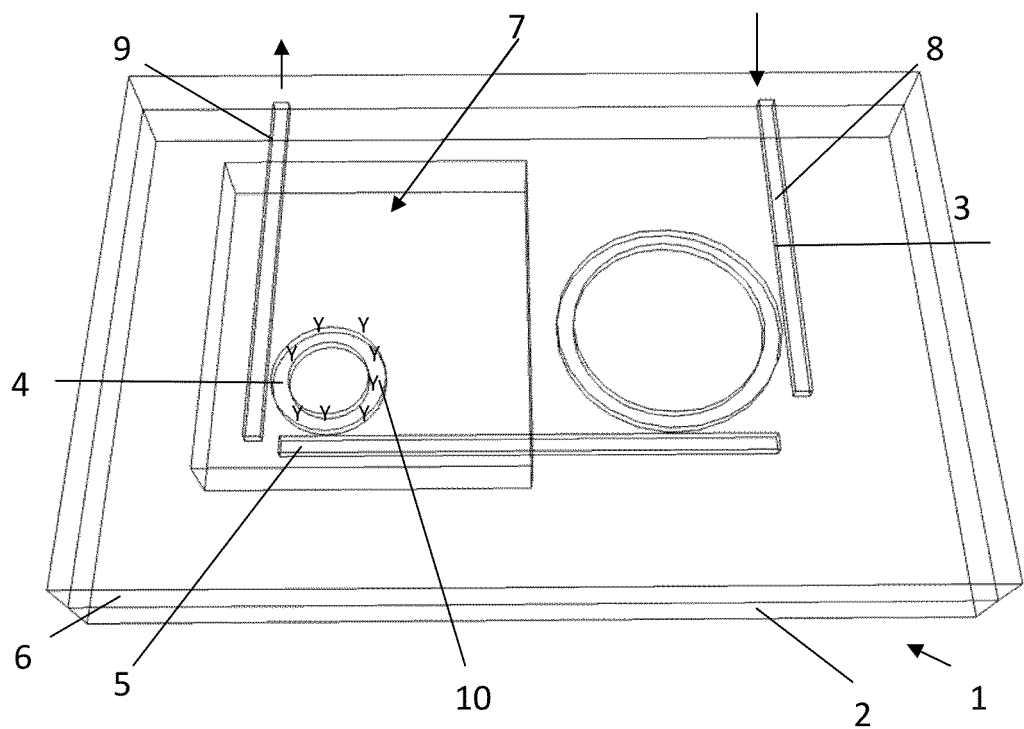
FIG. 1 – PRIOR ART
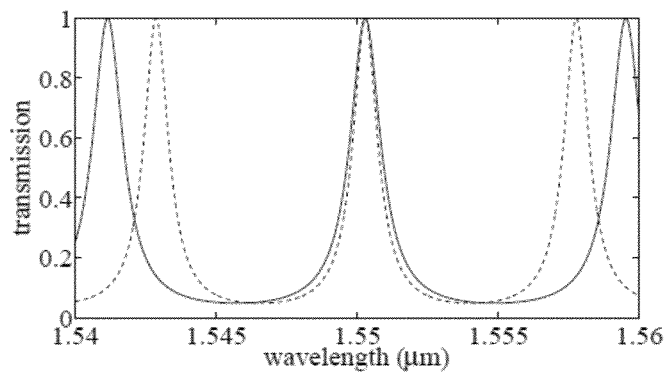
FIG. 2

VERNIER PHOTONIC SENSOR DATA-ANALYSIS

FIELD OF THE INVENTION

The invention relates to the field of photonic sensors. More specifically it relates to the field of sensors for sensing effective refractive index changes in a photonic sensor and methods for analyzing data thereof.

BACKGROUND OF THE INVENTION

Label-free photonic biosensors can be used for performing sensitive and quantitative multiparameter measurements on biological systems and can therefore contribute to major advances in medical analyses, food quality control, drug development and environmental monitoring. Additionally they offer the prospect of being incorporated in laboratories-on-a-chip that are capable of doing measurements at the point-of-care at an affordable cost.

A crucial component in most of these photonic biosensors is a transducer that can transform a refractive index change in its environment to a measurable change in an optical signal, e.g. an optical transmission signal. Silicon-on-insulator may be a material system with many assets for such transducers. First, it has a high refractive index contrast permitting very compact sensors of which many can be incorporated on a single chip, enabling multiplexed sensing. Second, silicon-on-insulator photonic chips can be made with CMOS-compatible process steps, allowing for a strong reduction of the chip cost for high volume fabrication. These sensor chips can therefore be disposable, meaning that the chip is only used once, avoiding complex cleaning of the sensor surface after use. Typically, a spectral shift of the transmission spectrum of the transducer is used to quantify the measured refractive index change. This method can be extended to the parallel read-out of multiple sensors in a sensor matrix.

For biosensors, the detection limit is an important figure of merit. The detection limit is defined as the ratio of the smallest detectable spectral shift and the sensitivity of the sensor. The latter is a measure for how much the spectrum shifts for a given change of the refractive index. There exist different types of transducers on silicon-on-insulator that use a variety of methods to achieve a low limit of detection. By using resonant sensors with high quality factors that have very narrow resonance peaks, the smallest detectable spectral shift can be minimized. Such sensors use a resonator, e.g. a ring resonator, which is exposed to a medium containing an analyte of interest. The sensors may have a surface which is adapted for the targeted analyte, e.g. which may comprise surface receptors for interacting with, e.g. temporarily or permanently binding, the target analyte. This interaction causes a local change in refractive index, which may influence the transmission spectrum of the resonator through the evanescent field, e.g. causing a wavelength offset in this spectrum.

Ring resonator sensors are known in the art, such ring resonators being made with mass fabrication compatible technology and having a detection limit as low as $7.6 \cdot 10^{-7}$ RIU. Such sensors may have a bulk sensitivity of 163 nm/RIU, which is not exceptionally high. However they may accomplish a smallest detectable wavelength shift as small as 0.22 pm with an optimized sensor design and a very noise resistant optical setup and data analysis. Slot waveguides with enhanced light-matter interaction may be applied to improve the sensitivity of ring resonator sensors with a factor two to four, but increased optical losses may prevented these sensors from achieving better detection limits than normal ring resonator sensors. Integrated interferometers with large interaction lengths may also have proved to be promising, with detection limits in the order of $10^{-6}$ RIU.

Furthermore, sensors are known in the art which consist of two ring resonators, arranged in cascade such that a high sensitivity may be achievable due to the Vernier-principle. The Vernier-scale is a method to enhance the accuracy of measurement instruments. It consists of two scales with different periods, of which one slides along the other one. The overlap between measurement marks on the two scales is used to perform the measurement. This scale is commonly used in callipers and barometers, and it has also found previous application in photonic devices, e.g. in the design of integrated lasers and tunable filters.

In D. Dai, "Highly sensitive digital optical sensor based on cascaded high-Q ring-resonators", Optics Express 2009 17 (26), such a Vernier-based sensor is disclosed. Referring to FIG. 1, such a Vernier-based sensor 1 may be implemented in Silicon-On-Insulator, for example comprising components patterned in silicon on an insulator layer 2 such as a silica layer. This sensor 1 comprises two ring resonators 3,4 with different optical roundtrip lengths, which are cascaded such that the drop signal of the first ring resonator is 3 coupled via a interconnecting waveguide 5 to the input of the second ring resonator 4, as illustrated in FIG. 1. The entire chip may be covered with a thick cladding 6, except for a region 7 in close proximity to one of the resonators, further referred to as the sensor ring resonator 4, where an opening is provided in the cladding so as to enable contacting the sensor ring resonator 4 to a test medium, for example this region 7 may be shaped such as to form a sample reservoir. This sensor ring resonator 4 will act as the sliding part of the Vernier-scale, as its evanescent field can interact with the refractive index in the environment of the sensor, where a change will cause a wavelength shift of the resonance spectrum. The other resonator, further referred to as the filter ring resonator 3, is shielded from these refractive index changes by the cladding and will act as the fixed part of the Vernier-scale. The cascade of both resonators can be designed such that a small shift of the resonance wavelengths of the sensor ring resonator will result in a much larger shift of the transmission spectrum of the cascade. Radiation may be coupled into the resonator cascade via an input waveguide 8, and collected from an output waveguide 9.

Each individual ring resonator has a comb-like transmission spectrum with peaks at its resonance wavelengths. The spectral distance between these peaks, the free spectral range, is inversely proportional to the optical roundtrip of the resonator. Therefore, each resonator in the cascade will have a different free spectral range, as illustrated by the transmission spectra of the filter ring resonator (dashed line) and of the sensor ring resonator (full line) shown in FIG. 2. As the transmission spectrum of the cascade of the two ring resonators, illustrated in FIG. 3, is the product of the transmission spectra of the individual resonators, it will only exhibit peaks at wavelengths for which two resonance peaks of the respective ring resonators at least partially overlap, and the height of each of these peaks will be determined by the amount of overlap. Thus, the cascade will have a spectral response with major peaks locating at the common resonant wavelengths of the cascaded rings.

However, this known sensor operates as a digital, i.e. a discrete, sensor, which limits the smallest detectable shift and the detection limit of the sensor. In such a discrete operating regime, the free spectral range difference between the two resonators in the cascade is large compared to the full-width at half-maximum of the resonance peaks of the individual resonators. The transmission spectrum of the cascade will then typically exhibit isolated peaks, of which the neighbouring peaks are inhibited. In such a discrete sensor, the transmission peak will hop from one filter ring resonance wavelength to another for a changing refractive index. The smallest detectable shift of the transmission spectrum of this sensor is therefore equal to the free spectral range of the filter ring resonator, which forms a limitation to the detection limit of the sensor.

SUMMARY OF THE INVENTION

It is an object of embodiments of the present invention to provide good and sensitive detection of refractive index changes in a medium.

It is an advantage of embodiments according to the present invention that a low detection limit of refractive index changes may be achieved.

It is an advantage of embodiments according to the present invention that bio-analytes may be characterized by analyzing changes of refractive index in a medium.

It is an advantage of embodiments according to the present invention that continuous sensing may be achieved, as opposed to discrete, e.g. digital, sensing.

It is an advantage of embodiments according to the present invention that the smallest detectable wavelength shift may be substantially lower than achievable by known discrete sensing techniques.

It is an advantage of embodiments according to the present invention that a large sensitivity may be achieved. It is a further advantage that embodiments of the present invention may be well suited for integration with on-chip dispersive elements such as arrayed waveguide gratings or planar concave gratings.

It is an advantage of embodiments according to the present invention that a cheap and portable sensor read-out may be provided.

The above objective is accomplished by a method and device according to the present invention.

The present invention relates to a method for quantifying an effective refractive index change in a photonic sensor and/or a method for quantifying an optical roundtrip length change of a photonic sensor, the method comprising the steps of obtaining spectral data representative for an optical signal being modulated with an optical transfer characteristics of the photonic sensor, the modulation being obtained by combining modulation of a first electromagnetic wave component in an optical filter element with a first periodic transfer spectrum having a first free spectral range and modulation of a second electromagnetic wave component in an optical filter element with a second periodic transfer spectrum having a second free spectral range being different from the first free spectral range, wherein a relative change is induced in the second periodic transfer spectrum with respect to the first periodic transfer spectrum as a result of changing environmental conditions or conformational changes of the photonic sensor, and quantifying the effective refractive index change of the photonic sensor taking into account said spectral data, characterized in that said quantifying comprises determining a wavelength offset of an envelope signal applied to the spectral data, the envelope signal having a wavelength periodicity substantially larger than a periodicity of the first periodic transfer spectrum and the second periodic transfer spectrum.

The optical filter element may be a resonator or interferometer. The electromagnetic wave component may be a mode, a degenerated mode, a combination of modes, etc.

The first periodic transfer spectrum and/or said second periodic transfer spectrum may be a comb filter.

Determining a wavelength offset of an envelope signal may comprise determining a plurality of wavelength locations corresponding to a plurality of peaks and/or valleys in said spectral data.

Determining a plurality of wavelength locations corresponding to a plurality of peaks and/or valleys may comprise identifying a plurality of intermittent peaks and/or valleys in said spectral data, and, for each pair of successive peaks and/or valleys, fitting a first function having a first wavelength location parameter to the spectral data obtained for wavelengths in the range defined by said pair of successive peaks and/or valleys, in order to obtain a plurality of first wavelength location parameter values and amplitude values.

The plurality of peaks may be selected such that the spectral data value corresponding to the peak wavelength exceeds a predetermined threshold value.

The first function may comprise a product of Lorentzian functions.

Determining a wavelength offset of an envelope signal further may comprise fitting a second function having a second wavelength location parameter to said plurality of first wavelength locations parameter values and amplitude values.

The second function may comprise a square of a Lorentzian function.

Fitting a second function may comprise a non-linear regression technique.

The fitting function may be or may comprise a product of Lorentzian functions.

The second electromagnetic wave component may be the modulated first electromagnetic wave component.

Obtaining the spectral data may comprise coupling a first electromagnetic wave into at least one optical filter element implemented on a photonic sensor, applying a modulation with a first periodic transfer spectrum to said first electromagnetic wave component using said at least one optical filter element, applying a modulation with a second periodic transfer spectrum to said second electromagnetic wave component using at least one optical filter element, the first and second periodic transfer spectrum having a different free spectral range, contacting the photonic sensor to a test medium such that the refractive index of the test medium influences a relative wavelength shift in the first periodic transfer spectrum with respect to the second periodic transfer spectrum.

Obtaining spectral data, the method further may comprise providing a photonic sensor, the photonic sensor comprising: an input waveguide structure for receiving a first electromagnetic wave, at least one optical filter element coupled to said input waveguide structure and configured for causing optical interference so as to apply said first modulating with said first periodic transfer spectrum and said second modulating with said second periodic transfer spectrum, and an output waveguide structure for coupling a combination of said first electromagnetic wave, modulated by the first periodic transfer spectrum, and said second electromagnetic wave, modulated by the second periodic transfer spectrum, out of the photonic sensor.

The difference between the first free spectral range and the second free spectral range may be smaller than or equal to a smallest full width at half maximum of the peaks in the first or second periodic transfer spectrum.

The photonic sensor may be adapted for, when contacting said photonic sensor to said test medium, enabling the refractive index of said test medium to influence an evanescent wave in said at least one optical filter element so as to generate a relative wavelength shift in the first periodic transfer spectrum with respect to the second periodic transfer spectrum.

The photonic sensor may comprise a first optical filter element being optically coupled in sequence to a second optical filter element, the first and second optical filter element being arranged such that the refractive index of said test medium influences a wavelength shift of the transmission spectrum of at least one of the first and second optical filter element, and the first optical filter element and second optical filter element have free spectral ranges differing such that a Vernier configuration is achieved.

The photonic sensor may comprise a waveguide arranged such that the evanescent field of electromagnetic radiation when propagating through this waveguide, or at least a part thereof, passes through a receptacle of the test medium, such that refractive index changes in the test medium influence the evanescent field and thus the propagation of electromagnetic radiation through the waveguide.

Combining may comprise applying a multiplication.

Obtaining spectral data may comprise obtaining data for a plurality of measurements of intensity, transmittance and/or absorbance.

The present invention also relates to a computer program product for, when executing on a processing unit, quantifying the refractive index of a test medium which is brought into contact with a photonic sensor, using a method as described above.

The present invention furthermore relates to a data carrier substrate comprising a computer program product as described above as well as to transmission of such a computer program product over a local area network or wide area network.

The present invention also relates to a processor for quantifying a refractive index of a test medium, the processor being programmed for determining a wavelength offset of an envelope signal in spectral data, the envelope signal having a wavelength periodicity substantially larger than a periodicity of the first periodic transfer spectrum and the second periodic transfer spectrum,
wherein said spectral data are representative for an optical signal being modulated with an optical transfer characteristics of a photonic sensor, the modulation being obtained by combining modulation of a first electromagnetic wave component in an optical filter element with a first periodic transfer spectrum having a first free spectral range and modulation of a second electromagnetic wave component in an optical filter element with a second periodic transfer spectrum having a second free spectral range being different from the first free spectral range, wherein a relative change is induced in the second periodic transfer spectrum by bringing the test medium in proximity with the optical filter element with the second periodic transfer spectrum.

The present invention also relates to a system for quantifying a refractive index of a test medium, the system comprising a processor as described above, the system furthermore comprising
a sensor comprising an input waveguide structure for receiving a first electromagnetic wave, at least one optical filter element coupled to said input waveguide structure and configured for causing optical interference so as to apply said first modulating with said first periodic transfer spectrum and said second modulating with said second periodic transfer spectrum, and an output waveguide structure for coupling a combination of said first electromagnetic wave, modulated by the first periodic transfer spectrum, and said second electromagnetic wave, modulated by the second periodic transfer spectrum, out of the photonic sensor, a light source for coupling a first electromagnetic wave into said at least one optical filter element and a detector for determining the spectral data.

Particular and preferred aspects of the invention are set out in the accompanying independent and dependent claims. Features from the dependent claims may be combined with features of the independent claims and with features of other dependent claims as appropriate and not merely as explicitly set out in the claims.

These and other aspects of the invention will be apparent from and elucidated with reference to the embodiment(s) described hereinafter.

BRIEF DESCRIPTION OF THE DRAWINGS

FIG. 1 illustrates a prior art photonic sensor comprising two cascaded ring resonators.

FIG. 2 shows exemplary transmission spectra for the two ring resonators, in isolation, of the sensor shown in FIG. 1.

Figure 3:
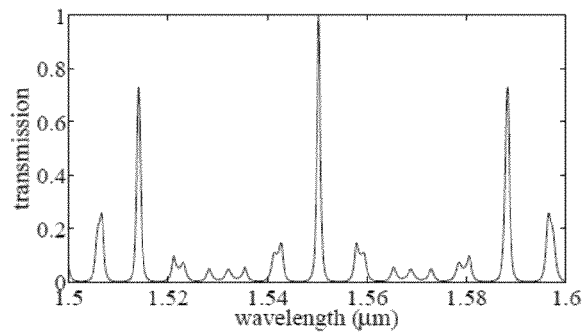
FIG. 3 shows a transmission spectrum corresponding to the two ring resonators, in cascade, of the sensor shown in FIG. 1.

The drawings are only schematic and are non-limiting. In the drawings, the size of some of the elements may be exaggerated and not drawn on scale for illustrative purposes.

Any reference signs in the claims shall not be construed as limiting the scope.

In the different drawings, the same reference signs refer to the same or analogous elements.

DETAILED DESCRIPTION OF ILLUSTRATIVE EMBODIMENTS

The present invention will be described with respect to particular embodiments and with reference to certain drawings but the invention is not limited thereto but only by the claims. The drawings described are only schematic and are non-limiting. In the drawings, the size of some of the elements may be exaggerated and not drawn on scale for illustrative purposes. The dimensions and the relative dimensions do not correspond to actual reductions to practice of the invention.

Furthermore, the terms first, second and the like in the description and in the claims, are used for distinguishing between similar elements and not necessarily for describing a sequence, either temporally, spatially, in ranking or in any other manner. It is to be understood that the terms so used are interchangeable under appropriate circumstances and that the embodiments of the invention described herein are capable of operation in other sequences than described or illustrated herein.

Moreover, the terms top, under and the like in the description and the claims are used for descriptive purposes and not necessarily for describing relative positions. It is to be understood that the terms so used are interchangeable under appropriate circumstances and that the embodiments of the invention described herein are capable of operation in other orientations than described or illustrated herein.

It is to be noticed that the term "comprising", used in the claims, should not be interpreted as being restricted to the means listed thereafter; it does not exclude other elements or steps. It is thus to be interpreted as specifying the presence of the stated features, integers, steps or components as referred to, but does not preclude the presence or addition of one or more other features, integers, steps or components, or groups thereof. Thus, the scope of the expression "a device comprising means A and B" should not be limited to devices consisting only of components A and B. It means that with respect to the present invention, the only relevant components of the device are A and B.

Reference throughout this specification to "one embodiment" or "an embodiment" means that a particular feature, structure or characteristic described in connection with the embodiment is included in at least one embodiment of the present invention. Thus, appearances of the phrases "in one embodiment" or "in an embodiment" in various places throughout this specification are not necessarily all referring to the same embodiment, but may. Furthermore, the particular features, structures or characteristics may be combined in any suitable manner, as would be apparent to one of ordinary skill in the art from this disclosure, in one or more embodiments.

Similarly it should be appreciated that in the description of exemplary embodiments of the invention, various features of the invention are sometimes grouped together in a single embodiment, figure, or description thereof for the purpose of streamlining the disclosure and aiding in the understanding of one or more of the various inventive aspects. This method of disclosure, however, is not to be interpreted as reflecting an intention that the claimed invention requires more features than are expressly recited in each claim. Rather, as the following claims reflect, inventive aspects lie in less than all features of a single foregoing disclosed embodiment. Thus, the claims following the detailed description are hereby expressly incorporated into this detailed description, with each claim standing on its own as a separate embodiment of this invention.

Furthermore, while some embodiments described herein include some but not other features included in other embodiments, combinations of features of different embodiments are meant to be within the scope of the invention, and form different embodiments, as would be understood by those in the art. For example, in the following claims, any of the claimed embodiments can be used in any combination.

In the description provided herein, numerous specific details are set forth. However, it is understood that embodiments of the invention may be practiced without these specific details. In other instances, well-known methods, structures and techniques have not been shown in detail in order not to obscure an understanding of this description.

Where in embodiments of the present invention reference is made to radiation, reference is made to electromagnetic radiation. The radiation envisaged is in principle not limited and may be any useful wavelength or wavelength range for detection or sensing applications envisaged. Some examples of radiation ranges that are envisaged, embodiments of the present invention not being limited thereto, are visual radiation, infrared radiation, near infrared radiation and mid infrared radiation.

Where in embodiments of the present invention reference is made to a photonics integrated circuit, reference is made to a variety of forms and material systems such as for example low-index contrast waveguide platforms, e.g. polymer waveguides, glass/silica waveguides, $Al_xGa_{1-x}As$ waveguides, $In_xGa_{1-x}As_yP_{1-y}$ waveguides or SiN waveguides, high-index contrast waveguide platforms, e.g. Silicon-on-Insulator or semiconductor membranes, or plasmonic waveguides, or waveguides based on silicon, germanium, silicon germanium, silicon nitride, silicon carbide, etc. Silicon-on-Insulator, is a very interesting material system for highly integrated photonic circuits. The high refractive index contrast allows photonic waveguides and waveguide components with submicron dimensions to guide, bend and control light on a very small scale so that various functions can be integrated on a chip. Such waveguides allow a high level of miniaturization, which is advantageous. Furthermore for such waveguide types radiation can be efficiently coupled in and out the photonics integrated circuit. Using Silicon-on-insulator also has some technological advantages. Due to the CMOS industry, silicon technology has reached a level of maturity that outperforms any other planar chip manufacturing technique by several orders of magnitude in terms of performance, reproducibility and throughput. Nano-photonic ICs can be fabricated with wafer scale-processes, which means that a wafer can contain a large number of photonic integrated circuits.

When in embodiments of the present invention reference is made to a photonics integrated circuit, reference is made to an optical circuit comprising at least one integrated optical component being an optical filter element, such as for example a resonator being a ring resonator or disk resonator or photonic crystal resonator or a Mach-Zehnder interferometer. Further components also may be integrated such as an integrated optical cavity, a further integrated optical resonator, an integrated optical interferometer, an integrated optical coupler, a waveguide, a taper, a tunable filter, a phase-shifter, a grating, a modulator, a detector, a light source or a combination thereof.

Where in embodiments of the present invention reference is made to the detection limit of a refractive index sensor, reference is made to the smallest change of the refractive index that can be detected, i.e. defined as the ratio between the smallest detectable spectral shift of the transmission spectrum of the sensor, as such referred to spectral resolution, and the sensitivity of the sensor. The sensitivity is indicative of the amount of shift in the transmission spectrum in the sensor for a given amount of targets to be sensed.

Where in embodiments of the present invention reference is made to the free spectral range, reference is made to a parameter corresponding with the period of the periodic transmission spectrum.

Where in the present invention reference is made to a changing environmental condition, reference is made to a change in temperature, a change in pH of a medium in contact with the sensor, a change due to a-specific binding, a change to specific binding, a change due to targets passing a sensor interface, etc.

Where in the present invention reference is made to conformal changes of the photonic sensor, the latter may refer for example to a change of the sensor due to stress or strain on the sensor, such as for example structural changes due to stress, etc.

Whereas embodiments of the present invention have been and will be further discussed mainly with reference to resonators, it should be understood that this equally applies to other type of filter elements, such as interferometers.

Figure 4:
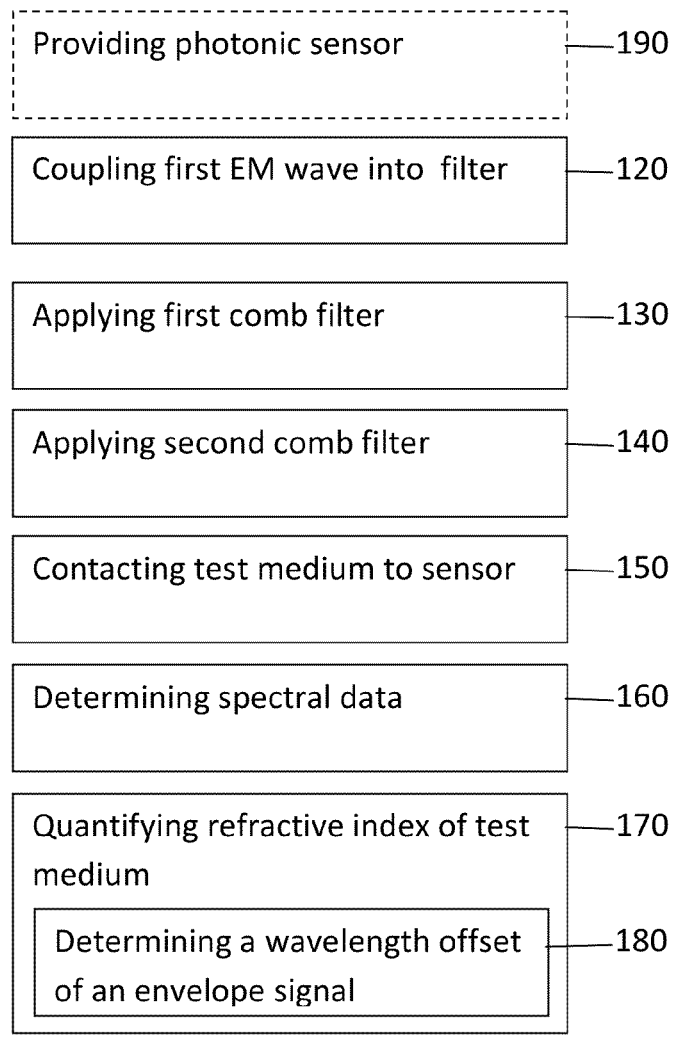
FIG. 4 shows an exemplary method for determining a refractive index of a test medium according to an embodiment of the first aspect of the present invention.

In a first aspect, the present invention relates to a method for quantifying an effective refractive index change in a photonic sensor. The method also may be referred to a method for quantifying an optical roundtrip length change of a photonic sensor. In some embodiments, the present invention particularly relate to methods for quantifying a refractive index change in a test medium or a refractive index change at or in a photonic sensor due to the binding of biological, chemical, biomimic or biochemical targets to an interface surface of the photonic sensor. The method according to embodiments of the present invention is especially suitable for being performed using a Vernier sensor, e.g. a Vernier integrated photonics sensor. The method typically comprises obtaining spectral data representative for an optical signal being modulated with an optical transfer characteristic of the photonics sensor used and for quantifying the effective refractive index change of the photonic sensor based on or taking into account the obtained spectral data. The modulated spectral data are such that the modulation is obtained by combining modulation of a first electromagnetic wave component in a resonator with a first periodic transfer spectrum having a first free spectral range and modulation of a second electromagnetic wave component in a resonator with a second periodic transfer spectrum having a second free spectral range being different from the first free spectral range. Furthermore the data is such that a relative change is induced in the second periodic transfer spectrum with respect to the first periodic transfer spectrum. The latter can be as a result of changing environmental conditions or conformational changes of the photonic sensor, e.g. by altering temperature, by bringing a medium in proximity with the resonator with the second periodic transfer spectrum, by applying a stress, . . . . Quantifying thereby comprises determining a wavelength offset of an envelope signal applied to or fitted to the spectral data, the envelope signal having a wavelength periodicity substantially larger than a periodicity of the first periodic transfer spectrum and the second periodic transfer spectrum. Further features and advantages will be discussed below, for ease of illustration with reference to an exemplary method 100 shown in FIG. 4. This method 100 comprises obtaining spectral data 160, which may be performed either by receiving the data as previously stored data via a data input, or it may be data stemming directly from a measurement. The spectral data may correspond with measurements of an optical transfer characteristic of the photonic sensor as function of wavelength, for example measurements which comprise a plurality of measurements of intensity, transmittance and/or absorbance. For example, in this plurality of measurements, each measurement may correspond with a wavelength or wavelength range of electromagnetic radiation propagating through the photonic sensor for which the measurement is obtained. Each measurement may then be a property of this electromagnetic radiation in such wavelength range or at such a wavelength, for example a measurement of intensity, transmittance or absorption.

In one embodiment, obtaining spectral data therefore also comprises coupling 110 a first electromagnetic wave into at least one resonator, e.g. integrated filter element, implemented on a photonic sensor and applying 130 a modulation with a first periodic transfer spectrum having a first free spectral range to the first electromagnetic wave using at least one resonator. The first periodic transfer spectrum modulation may be a first optical comb filtering operation applied to the first electromagnetic wave using said at least one integrated filter element. Obtaining spectral data then also encompasses applying 140 a second periodic transfer spectrum modulation to the second electromagnetic wave component using a resonator. The second periodic transfer spectrum modulation has a second free spectral range being different from the first free spectral range. The second periodic transfer spectrum modulation may be an optical comb filtering operation, applied to the second electromagnetic wave using a resonator. This different free spectral range may be chosen such that a measurement regime is enabled which is distinct from the measurement regime disclosed in the prior art publications discussed in the background section hereinabove. The difference in these free spectral ranges advantageously may be selected to be small. The difference in the free spectral ranges may be smaller than the largest full width at half maximum of the peaks in the periodic transfer spectra, i.e. the largest full width at half maximum (of the peaks) in the first periodic transfer spectrum and the second periodic transfer spectrum. Selecting the difference in free spectral ranges small the latter results in a more distinct shift of the envelope function that will occur.

The second electromagnetic wave may correspond with the first electromagnetic wave being modulated with the first periodic transfer spectrum. It thus may be a wave coupled out of the first resonator and subsequently send to the second resonator.

In the event, obtaining the spectral data comprises obtaining through measurement, the method 100 may comprise the step of providing 190 the photonic sensor. For example, this photonic sensor may be similar in design to the prior art sensor shown in FIG. 1, e.g. may comprise a transducer based on the Vernier principle, but may use ring resonators with very large roundtrip lengths in order to enable another regime in order to improve the detection limit. In this regime, the detection limit of e.g. silicon-on-insulator label-free biosensors may be enhanced while maintaining a very simple circuit design, compatible with mass fabrication technology, and being suitable for a high degree of multiplexing. While a straightforward approach is using ring resonators as sensor element, however, the invention is not intended to be limited thereto, and a method according to the first aspect of the present invention may works with other filtering elements, such as FP-resonators or other optical resonators, as well. The photonic sensor may comprise an input waveguide structure 7 for receiving the first electromagnetic wave. The photonic sensor may further comprise at least one integrated filter element 3,4 coupled to the input waveguide structure 7 and configured for causing optical interference so as to apply the first optical comb filtering operation and the second optical comb filtering operation. The photonic sensor may comprise an output waveguide structure 8 for coupling a superposition of the first electromagnetic wave, having the first optical comb filtering operation applied thereto, and the second electromagnetic wave, having the second optical comb filtering operation applied thereto, out of the photonic sensor. For example, when the at least one integrated filter element comprises two filter elements 3,4 interconnected in a cascade configuration, the first electromagnetic wave may consecutively be coupled into the first filter element 3, have a first optical filtering operation applied thereto, be coupled into the second filter element 4 by a interconnecting waveguide 5, have a second optical filtering operation applied thereto, and finally be coupled out of the photonic sensor by the output waveguide structure 8. Therefore, in this exemplary serial configuration, a multiplicative superposition of the first electromagnetic wave and the second electromagnetic wave may be coupled out of the photonic sensor.

When obtaining the spectral data by measurement, the method 100 further may comprise the step of contacting 150 the photonic sensor to a test medium such that the refractive index of the test medium influences a relative wavelength shift between the spectral response to the first periodic transfer spectrum and the spectral response to the second periodic transfer spectrum. For example, the photonic sensor may be adapted for, when contacting 15 the photonic sensor to the test medium, enabling the refractive index of the test medium to influence an evanescent wave in the at least one filter element 3,4 so as to generate a relative wavelength shift between the spectral response to the first periodic transfer spectrum, e.g. the first optical comb filtering operation, and the spectral response to the second periodic transfer spectrum, e.g. the second optical comb filtering operation. Therefore, the photonic sensor may be sensitive to refractive index changes in the test medium, e.g. such changes as induced by analytes of interest, e.g. biological, chemical or bio-chemical agents which may be bound to a surface of the photonic sensor by purposefully designed receptor molecules. The photonic sensor may comprise a waveguide arranged such that the evanescent field of electromagnetic radiation propagating through this waveguide, or at least a part thereof, may pass through a receptacle of this test medium, e.g. such that refractive index changes in the medium influence the evanescent field and consequently the propagation of electromagnetic radiation through the waveguide. Alternatively or in addition thereto, the change in effective refractive index also may be performed by changing environmental conditions, or changing conformational conditions for the photonic sensor, such as inducing stress or strain.

In one particular embodiment, the photonic sensor may comprise a first resonator being optically coupled in sequence to a second resonator, in which the first and second resonator may be arranged such that the refractive index of the medium influences a wavelength shift of the transmission spectrum of at least one of the first and second resonator, and the first resonator and second resonator have free spectral ranges differing such that a Vernier configuration is achieved. The photonic sensor may comprise a waveguide arranged such that the evanescent field of electromagnetic radiation propagating through this waveguide, or at least a part thereof, may pass through a receptacle for the test medium, such that refractive index changes in the medium influence the evanescent field and thus the propagation of electromagnetic radiation through the waveguide. The resonant wavelengths of the at least one integrated filter element, i.e. of the first and second optical comb filtering operation, may for example be precisely controlled by tuning or trimming, or applying high resolution technology in the production process of such photonic sensors.

The method 100 also comprises the step of quantifying 170 the refractive index of the test medium taking into account said spectral data. This quantifying 170 comprises determining 180 a wavelength offset of an envelope signal in said spectral data. This envelope signal has a wavelength periodicity substantially larger than the spectral response periodicity of the first and the second periodic transfer spectrum. In methods according to the present invention, an analytical formula for this envelope signal may be used, which can be fitted to experimental data, making it possible to continuously track the spectrum of the sensor, thus allowing a sensitive detection limit. In order to work in this regime, the optical resonators used for determining the spectral data typically need to have a large optical roundtrip in order to have a small free spectral range.

Determining 180 a wavelength offset may comprise determining a plurality of wavelength locations corresponding to a plurality of peaks in the spectral data. For example, a plurality of intermittent peaks and/or valleys in the determined 180 spectral data may be identified. This may comprise any suitable technique for identifying such peaks and/or valleys, for example computing a gradient, e.g. a discrete approximation of the wavelength derivative. This may also comprise any suitable numeric filtering technique to avoid detecting peaks which are due to noise in the spectral data, for example applying convolution with a smoothing kernel, a Fourier transform and multiplication by a transfer function in the Fourier domain, a wavelet transform and scaling of wavelet coefficients, and/or a hierarchical signal segmentation techniques. The method may comprise selection of such detected peaks based on a predetermined threshold value, e.g. inclusion of such peaks when the spectral data value corresponding to the peak wavelength exceeds this predetermined threshold value and exclusion of peaks which fall below this value. This may offer the benefit of an improved robustness to noise, i.e. when considering the envelope signal present in the spectral data, only the central range having good noise to signal properties may be selected.

The determining 180 may further comprise, for each pair of successive valleys, fitting a first function having a first wavelength location parameter to the spectral data obtained for wavelengths in the range defined by this pair of successive valleys. For example, this first function may be a product of Lorentzian functions, e.g.

$$T(\lambda) = t_{max} w^2 \frac{1}{w^2 + 4\left(\lambda - \lambda_0 - \frac{\Delta\lambda}{2}\right)^2} \cdot \frac{1}{w^2 + 4\left(\lambda - \lambda_0 + \frac{\Delta\lambda}{2}\right)^2}$$

in which $t_{max}$ is an amplitude parameter, w is a full-width at half-maximum, $\Delta\lambda$ is a wavelength separation distance and $\lambda_0$ is said first wavelength location parameter. If the first and second periodic transfer spectrum are implemented in the at least one integrated filter element by a cascade of two ring resonators, both having resonance peaks of substantially equal full-width at half-maximum w, then the amplitude parameter $t_{max}$ may be the product of the transmissions at resonance for both ring resonators. In such case, a pair of at least partially overlapping resonance peaks of respectively the first and second ring resonator may be separated by $\Delta\lambda$. Fitting this exemplary function to an observed peak, e.g. such a peak as would be observed from multiplicative superposition of a pair of at least partially overlapping resonance peaks of the ring resonators, may yield parameter values for the wavelength location parameter $\lambda_0$, wavelength separation distance $\Delta\lambda$, amplitude parameter $t_{max}$ and full-width at half maximum w. Alternatively, a predetermined value for the full-width at half-maximum w may be used instead of a fitted value. The fitting procedure may involve any suitable method for functional fitting, for example, a non-linear ordinary or total least squares method may be used, a least absolute deviation method, or any numerical optimization technique for minimizing a distance metric. In such way, a plurality of first wavelength location parameter values $\{\lambda_0\}_{i=1,\ldots,n}$ may be obtained, and with each first wavelength location parameter value $\lambda_{0,i}$ an amplitude value may be associated by evaluating the first function for the fitted parameters and at a wavelength $\lambda$ equal to the wavelength location parameter value $\lambda_0$: e.g.

$$T_{max} = T(\lambda_0) = t_{max} \cdot \left(\frac{w^2}{w^2 + \Delta\lambda^2}\right)^2.$$

The determining 180 a wavelength offset of an envelope signal may also comprise fitting a second function having a second wavelength location parameter to this plurality of wavelength locations and associated values of the fitted first functions at this plurality of wavelength locations. For example, the set of wavelength location parameters and corresponding peak amplitudes $\{(\lambda_{0,i}, T_{max,i})\}_{i=1,\ldots,n}$ obtained for a set of n peaks as described above, may be used to fit a second function, for example a square of a Lorentzian function, e.g.

$$T_{envelope}(\lambda) = t_{max}\left(\frac{W^2}{W^2 + 4(\lambda - \lambda_{central})^2}\right)^2,$$

in which W is a full-width half-maximum parameter of the envelope signal, and $\lambda_{central}$ is the second wavelength location parameter. This fitting may again comprise any suitable method for functional fitting, for example, a non-linear regression technique, such as a non-linear ordinary or total least squares method, a least absolute deviation method, or any numerical optimization technique for minimizing a distance metric.

Alternatively or in addition thereto, the determining 180 a wavelength offset of an envelope signal may comprise fitting a third function having a third wavelength location parameter to said spectral data, in which this third function is a convolution of a square of a Lorentzian function and a product of Lorentzian functions. In such way, a single fitting operation may be sufficient to determine this third wavelength location parameter, although the fitting function will be more complex, and as such may add to the computational complexity.

Additionally, instead of products of Lorentzian in the first step and/or the square of Lorentzian functions in the second step, more involved parametrised models can be used to capture additional aspects of the physical behaviour of the device, e.g. to include the band limiting effects of incoupling and outcoupling grating, the effects of backscattering in the ring, non-linear effects, . . . .

Based on the determined wavelength shift, a change in effective refractive index may be determined or even the presence of conditions causing the effective refractive index may be derived. The latter can for example be based on a look up table, a neural network, a predetermined algorithm, previously performed calibration measurements, etc. This may allow directly deriving a qualitative characterisation or even a quantitative characterisation of the presence of analytes, the presence of stress, the change in temperature, the change in pH, . . . based on the wavelength shift of the envelope.

In a second aspect, the present invention relates to a processor for quantifying an effective refractive index change in a photonic sensor. The processor also may be referred to as a processor for quantifying an optical roundtrip length change of a photonic sensor. In some embodiments, the present invention particularly relate to a processor for quantifying a refractive index change in a test medium or a refractive index change at or in a photonic sensor due to the binding of biological, chemical, biomimic or biochemical targets to an interface surface of the photonic sensor. The processor thereby is programmed for determining a wavelength offset of an envelope signal in spectral data. These spectral data comprise measurements of an optical transfer characteristic of a photonic sensor as function of wavelength. The envelope signal having a wavelength periodicity substantially larger than a periodicity of the first periodic transfer spectrum and the second periodic transfer spectrum. The spectral data used for processing are representative for an optical signal being modulated with an optical transfer characteristics of a photonic sensor, the modulation being obtained by combining modulation of a first electromagnetic wave component in a resonator, e.g. filtering element, with a first periodic transfer spectrum having a first free spectral range and modulation of a second electromagnetic wave component in a resonator, e.g. filtering element, with a second periodic transfer spectrum having a second free spectral range being different from the first free spectral range, wherein a relative change is induced in the second periodic transfer spectrum by bringing the test medium in proximity with the resonator with the second periodic transfer spectrum. The processor may be implemented in hardware as well as in software. It may be programmed based on predetermined algorithms, make use of look up tables, use a neural network, etc. The processor may obtain the necessary input via an input port and may comprise memory and processing power for performing the processing. The output may be a wavelength offset in the envelope. Alternatively, the processor may be adapted for determining, based on the wavelength offset in the envelope, additional information regarding the medium, e.g. the change in refractive index causing the wavelength offset. Furthermore, based on calibration experiments, look up tables, etc. the processor may be adapted for determining, based on the wavelength offset in the envelope, a presence of analytes in a medium or a composition of the medium can be determined.

In a third aspect, the present invention relates to a computer program product for, when executing on a processing unit, e.g. such as a processing unit in a device according to the second aspect of the present invention, quantifying an effective refractive index change in a photonic sensor. The computer program product may be adapted for performing a method as described in the second aspect of the present invention. The computer program product may be adapted for quantifying the refractive index of a test medium of a photonic sensor, wherein the photonic sensor comprises resonators for providing a first and second periodic transfer spectrum modulation, such that the refractive index of the photonic sensor or at a surface interface there of influences a relative wavelength shift between the spectral responses of respectively the first and second transfer spectrum modulation for radiation in the sensor. The computer program product comprises programming code for determining a wavelength offset of an envelope signal in spectral data. The spectral data comprises measurements of an optical transfer characteristic of this photonic sensor as function of wavelength, and the envelope signal has a wavelength periodicity substantially larger than the spectral response periodicity of the first and second optical comb filtering operation. Particularly, this computer program product is adapted for partially implementing a method according to the first aspect of the present invention, e.g. the step of quantifying the refractive index of a test medium.

In a fourth aspect, the present invention relates to a system for quantifying an effective refractive index of a photonic sensor. The system comprises a photonic sensor and a processor as described above. This photonic sensor comprises at least one resonator adapted for applying a first periodic transfer spectrum modulation and applying a second periodic transfer spectrum modulation, in which the first and second periodic transfer spectra have a different free spectral range, also referred to as a different spectral response periodicity. For example the at least one resonator may comprise two ring resonators having different free spectral ranges. The system furthermore comprises a radiation source for coupling a first electromagnetic wave into this at least one integrated filter element, and a detector for determining spectral data comprising measurements of an optical transfer characteristic of the photonic sensor as function of wavelength when contacting the photonic sensor to a test medium such that the refractive index of the test medium influences a relative wavelength shift between the spectral response of the first transfer spectrum modulation and the spectral response of the second transfer spectrum modulation.

The system furthermore comprises a processing unit for quantifying the refractive index of the test medium taking into account this spectral data. The processing unit may be according to the processor as described above.

Theoretical principles of the present invention will further be presented in the description below in order to clarify aspects thereof. However, the invention is not intended to be limited by such principles in any way, nor by the particular mathematical formalism used.

In the prior-art regime of a digital, i.e. a discrete, sensor discussed in the background section hereinabove, the free spectral range difference between the two resonators in the cascade is large compared to the full-width at half-maximum of the resonance peaks of the individual resonators. In this regime, the transmission spectrum peak will hop from one filter ring resonance wavelength to the another for a changing refractive index.

Figure 5:
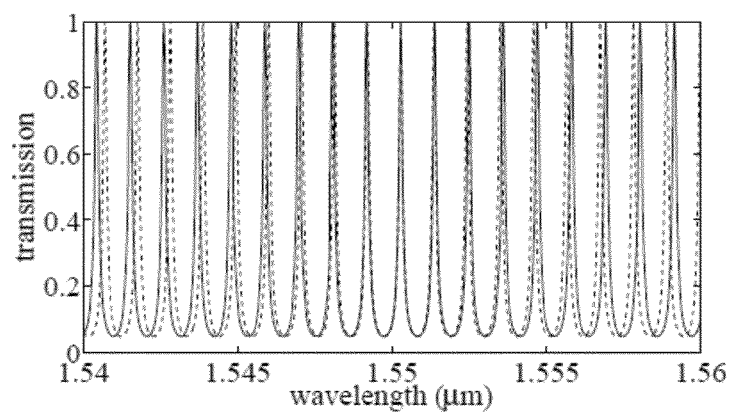
FIG. 5 shows exemplary transmission spectra for two ring resonators, in isolation, of a sensor suitable for use in a method according to an embodiment of the present invention.
Figure 6:
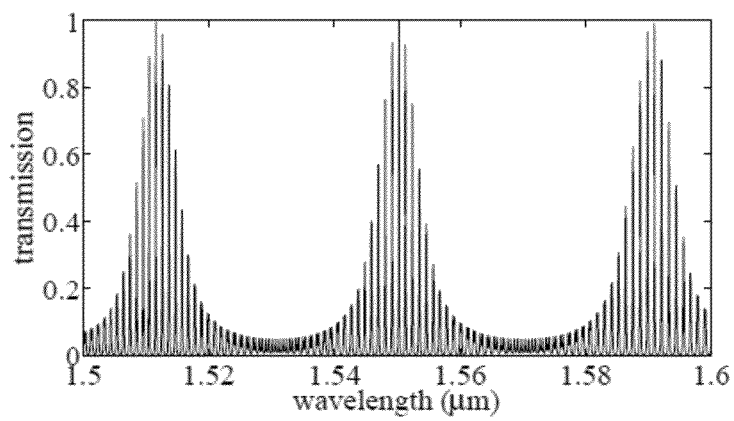
FIG. 6 shows a transmission spectrum corresponding to the two ring resonators, with spectra shown in FIG. 5, in cascade, as used in a method according to an embodiment of the present invention.

Embodiments of the present invention relate to another regime, which occurs when the free spectral range difference between the two resonators in the cascade is small compared to the full-width at half-maximum of the resonance peaks of the individual resonators. In FIG. 5, transmission spectra for such a sensor ring resonator (full line) and a filter ring resonator (dashed line) are illustrated. As shown in FIG. 6, in this regime a periodic envelope signal is superposed on the constituent transmission peaks. If dispersion is not taken into account, the envelope period is given by $$\frac{fsr_{sensor} \cdot fsr_{filter}}{|fsr_{sensor} - fsr_{filter}|},$$

where $fsr_{sensor}$ and $fsr_{filter}$ are the free spectral range values of the sensor ring resonator and the filter ring resonator respectively. This can be seen by assuming that at a wavelength $\lambda_0$ two resonances of the respective resonators coincide. Neglecting dispersion, the other resonance wavelengths of the resonators are: $\lambda_{sensor,k} = \lambda_0 + k \cdot fsr_{sensor}$ and $\lambda_{filter,k} = \lambda_0 + k \cdot fsr_{filter}$, in which k is an integer index. Assuming that $fsr_{filter} < fsr_{sensor}$ and $fsr_{sensor} - fsr_{filter} \ll fsr_{filter}$, starting from $\lambda_0$, an envelope period will be reached when two resonances coincide again. This occurs for an index k=K, for which:

$$\lambda_{sensor,K} = \lambda_{filter,K+1} \Leftrightarrow K \cdot fsr_{sensor} = (K+1) fsr_{filter} \Leftrightarrow K = \frac{fsr_{filter}}{fsr_{sensor} - fsr_{filter}}.$$

The two resonances will only exactly coincide when K is an integer, but when the free spectral range difference between the two resonators in the cascade is small compared to the full-width at half-maximum of the resonance peaks of the individual resonators this period will also be visible when K is not an integer. The expression for the envelope period can thus be obtained:

$$\lambda_{sensor,K} - \lambda_0 = \frac{fsr_{sensor} \cdot fsr_{filter}}{|fsr_{sensor} - fsr_{filter}|}.$$

Note that the envelope period may not be larger than the available wavelength range of the measurement equipment, so that this regime may require that the cascade consists of resonators with very large roundtrips The free spectral range difference between the two free spectral ranges advantageously is smaller than or equal to the largest of the full width at half maximum values of the periodic transfer spectra.

It can be proven that the resonance peaks in the drop spectrum of a single ring resonator can each individually be described in good approximation by a Lorentzian function:

$$T_{drop}(\lambda) = \frac{t_{max} \frac{fwhm^2}{4}}{\frac{fwhm^2}{4} + (\lambda - \lambda_{res})^2},$$

with $t_{max}$ the transmission at resonance, fwhm the full-width at half-maximum of the resonance peak and $\lambda_{res}$ the resonance wavelength.

As each peak in the transmission spectrum of the individual ring resonators may be approximated by a Lorentzian function, each of these constituent peaks in the transmission spectrum of the cascade can be described as the product of two Lorentzian functions that have a slightly different resonance wavelength, e.g. are shifted compared to each other:

$$T_{constituent}(\lambda) = \frac{t_{max,filter} \frac{fwhm_{filter}^2}{4}}{\frac{fwhm_{filter}^2}{4} + \left(\lambda - \lambda_0 - \frac{\Delta\lambda}{2}\right)^2} \cdot \frac{t_{max,sensor} \frac{fwhm_{sensor}^2}{4}}{\frac{fwhm_{sensor}^2}{4} + \left(\lambda - \lambda_0 + \frac{\Delta\lambda}{2}\right)^2},$$

where $t_{max}$ and fwhm are respectively the transmission at resonance and the full-width at half-maximum of the corresponding individual ring resonator, and where $\lambda_0$ and $\Delta\lambda$ are respectively the mean of and the difference between the two resonance wavelengths under consideration from both combs.

If we assume that both ring resonators in the cascade have the same full-width at half-maximum fwhm, this can be written as:

$$T_{constituent}(\lambda) = \frac{\sqrt{t_{max,filter} \cdot t_{max,sensor}} \frac{fwhm^2}{4}}{\frac{fwhm^2}{4} + \left(\lambda - \lambda_0 - \frac{\Delta\lambda}{2}\right)^2} \cdot \frac{\sqrt{t_{max,filter} \cdot t_{max,sensor}} \frac{fwhm^2}{4}}{\frac{fwhm^2}{4} + \left(\lambda - \lambda_0 - \frac{\Delta\lambda}{2}\right)^2}.$$

The location of the extreme values of this function can be found by solving the following equation to $\lambda$:

$$\frac{\partial T_{constituent}(\lambda)}{\partial \lambda} = 0.$$

This results in three extreme values at wavelengths:

$$\lambda_0, \lambda_0 - \frac{\sqrt{\Delta\lambda^2 - fwhm^2}}{2}, \lambda_0 + \frac{\sqrt{\Delta\lambda^2 - fwhm^2}}{2}.$$

This allows us to evaluate the location and values of the maxima of the constituent peaks, and two different shapes of the constituent peaks, depending on their position in the envelope peak, may be identified.

If the difference between the resonance wavelengths under consideration is larger than the full-width at half-maximum of the individual resonances, $\Delta\lambda > fwhm$, the three extreme values are real-valued. The corresponding constituent peak will in this case have two maxima, at $$\lambda_0 \pm \frac{\sqrt{\Delta\lambda^2 - fwhm^2}}{2},$$

and a local minimum at $\lambda_0$. The transmission of each of the maxima is $$T_{max} = \left(\frac{\sqrt{t_{max,filter} \cdot t_{max,sensor}} \, fwhm}{2\Delta\lambda}\right)^2,$$

which quickly converges to zero for increasing values of $\Delta\lambda$. This situation corresponds to the tails of the envelope, where the transmission is very low.

If however the difference between the resonance wavelengths under consideration is smaller or equal than the full-width at half-maximum of the individual resonators, $\Delta\lambda \leq fwhm$, only one of the extreme values is real-valued. This situation corresponds to the constituent peaks in the centre of the envelope peak, where the transmission is high. In this case the constituent peak has a maximum at its central wavelength $\lambda_0$ and the transmission at this maximum is given by $$T_{max} = \left(\frac{\sqrt{t_{max,filter} \cdot t_{max,sensor}} \, fwhm}{fwhm^2 + \Delta\lambda^2}\right)^2.$$

When the free spectral range difference between the two resonators in the cascade is small compared to the full-width at half-maximum of the resonance peaks of the individual resonators, a periodic envelope signal is superposed on the constituent transmission peaks in the transmission spectrum of the cascade. In every envelope period, there is an envelope peak that is composed of the highest constituent peaks, for which $\Delta\lambda \leq fwhm$, where each constituent peak has a maximum given by the expression hereabove.

Figure 12:
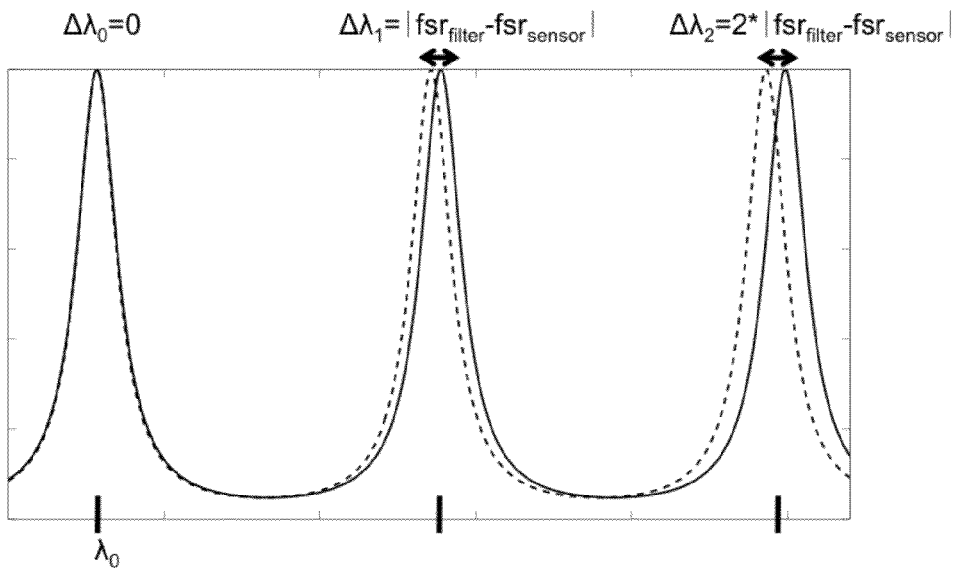
FIG. 12 illustrates individual transmission spectra of two resonators, illustrating features and advantages of embodiments of the present invention.
Figure 13:
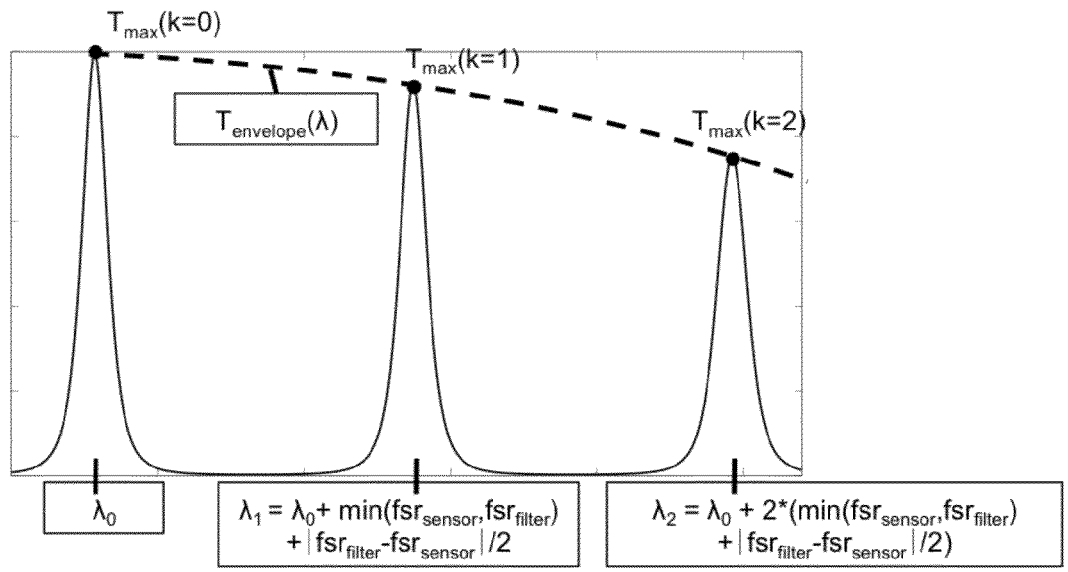
FIG. 13 illustrates a transmission spectrum of a cascade of the two resonators referred to in FIG. 12, illustrating features and advantages of embodiments of the present invention.

First the special case displayed in FIG. 12 and FIG. 13 will be considered, where there exists a wavelength $\lambda_0$ at which a resonance peak of the filter ring resonator, shown in solid line in FIG. 12, coincides with a resonance peak of the sensor ring resonator, shown in dashed line in FIG. 12. At this wavelength $\lambda_0$, it holds that $\Delta\lambda = 0$ and the corresponding constituent peak in the transmission spectrum of the cascade will reach the maximum height of the envelope signal. For the next resonance peak of both resonators, the resonance wavelength difference is equal to the difference in free spectral range, $\Delta\lambda_1 = |fsr_{sensor} - fsr_{filter}|$. As proven hereinabove, the corresponding constituent peak will have a maximum at the mean resonance wavelength, $\lambda_1 = \lambda_0 + \min(fsr_{sensor}, fsr_{filter}) + \frac{1}{2}|fsr_{sensor} - fsr_{filter}|$.

This reasoning can be generalized to all constituent peaks of the same envelope peak:

$\Delta\lambda_k = k \cdot |fsr_{sensor} - fsr_{filter}| \lambda_k = \lambda_0 + k \cdot (\min(fsr_{sensor}, fsr_{filter}) + \frac{1}{2}|fsr_{sensor} - fsr_{filter}|)$ where k is an integer. By combining these equations, we get:

$$\Delta\lambda_k = \frac{|fsr_{sensor} - fsr_{filter}|}{\min(fsr_{sensor}, fsr_{filter}) + \frac{1}{2}|fsr_{sensor} - fsr_{filter}|} |\lambda_k - \lambda_0|.$$

The second term in the denominator is typically much smaller than the first, so we can neglect the second term:

$$\Delta\lambda_k \approx \frac{|fsr_{sensor} - fsr_{filter}|}{\min(fsr_{sensor}, fsr_{filter})} |\lambda_k - \lambda_0|.$$

Substitution of this expression in the earlier introduced expression for $T_{max}$ yields:

$$T_{max}(k) = \left(\frac{\sqrt{t_{max,filter} \cdot t_{max,sensor}} \left(\frac{FWHM}{2}\right)^2}{\left(\frac{FWHM}{2}\right)^2 + (\lambda_k - \lambda_0)^2}\right)^2,$$

in which $$FWHM = 2 \cdot \frac{fwhm \cdot \min(fsr_{sensor}, fsr_{filter})}{|fsr_{filter} - fsr_{sensor}|}.$$

This formula gives the peak transmission values of the highest constituent peaks in the central region of the envelope peak, for the special case where there exists a constituent peak that is the product of two coinciding resonance peaks.

This may be generalized to the formula of a continuous function going through the maxima of the constituent peaks, also for the case where there is no perfect coincidence of resonances, by defining $\lambda_{central}$ as the central wavelength of the envelope peak and by substituting $\lambda_0$ and $\lambda_k$ respectively by $\lambda_{central}$ and the continuous wavelength $\lambda$:

$$T_{envelope}(\lambda) = \left( \frac{\sqrt{t_{max,filter} \cdot t_{max,sensor}} \left(\frac{FWHM}{2}\right)^2}{\left(\frac{FWHM}{2}\right)^2 + (\lambda - \lambda_{central})^2} \right)^2,$$

with $$FWHM = 2 \cdot \frac{fwhm \cdot \min(fsr_{sensor}, fsr_{filter})}{|fsr_{filter} - fsr_{sensor}|}.$$

This equation for $T_{envelope}(\lambda)$ shows that the envelope signal forms a peak described by the square of a Lorentzian function with full-width at half-maximum FWHM.

A change of the refractive index in the evanescent field of the sensor ring resonator will cause a shift of the resonance peaks in its transmission spectrum, which will be translated in a much larger shift of the central wavelength of the envelope peak in the transmission spectrum of the cascade.

Figure 14:
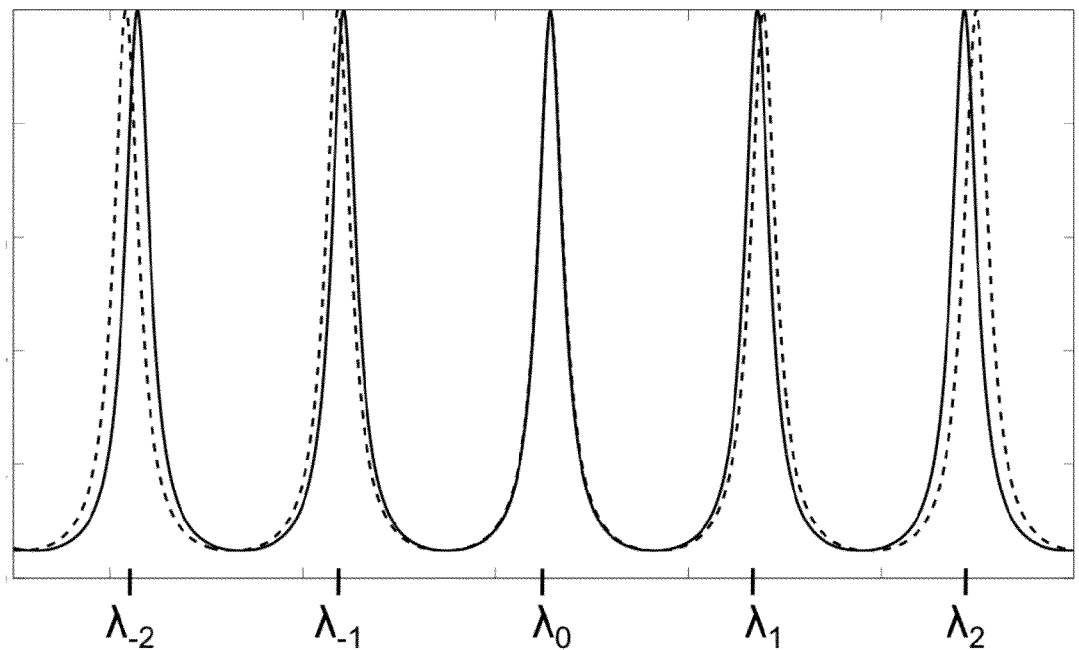
FIG. 14 shows transmission spectra of the individual filter ring resonator and sensor ring resonator for the case where two resonances of the respective resonators coincide at $\lambda_0$ and the free spectral range of the filter resonator is larger than the free spectral range of the sensor resonator, illustrating features and advantages of embodiments of the present invention.
Figure 15:
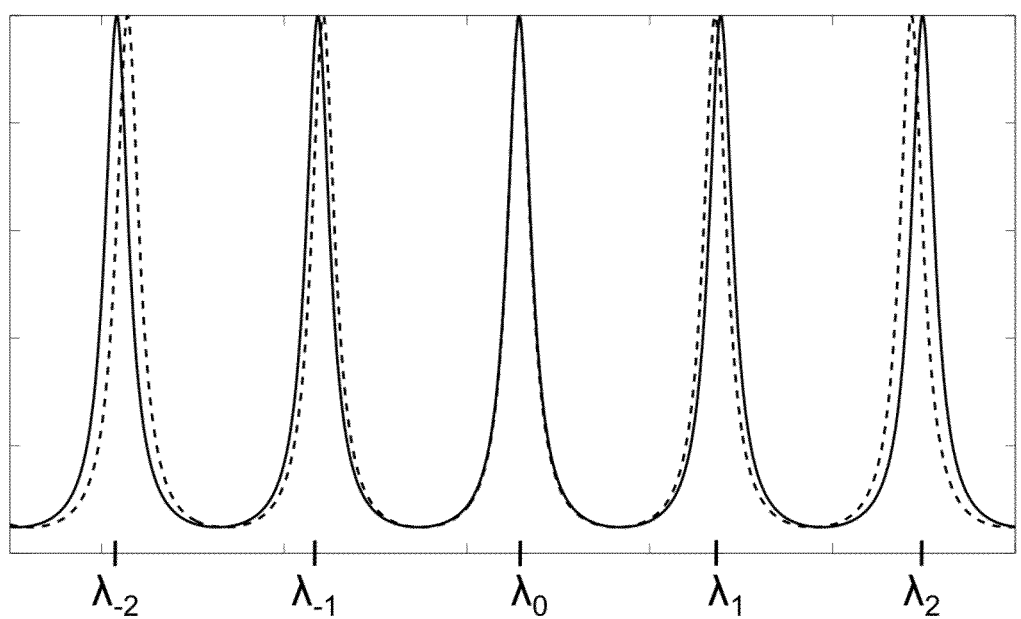
FIG. 15 shows transmission spectra of the individual filter ring resonator and sensor ring resonator for the case where two resonances of the respective resonators coincide at $\lambda_0$ and the free spectral range of the filter resonator is smaller than the free spectral range of the sensor resonator, illustrating features and advantages of embodiments of the present invention.

The special case shown in FIG. 14 and FIG. 15 also is considered, where there exists a wavelength $\lambda_0$ at which a resonance peak of the filter ring resonator (solid line) coincides with a resonance peak of the sensor ring resonator (dashed line). At this wavelength $\lambda_0$ the corresponding constituent peak in the transmission spectrum of the cascade will reach the maximum height of the envelope signal.

Two cases may be distinguished. The first case is illustrated in FIG. 14, and occurs when the free spectral range of the filter resonator is larger than the free spectral range of the sensor resonator. When in this case the resonance wavelengths of the sensor ring resonator shift to larger wavelengths over a spectral distance $|fsr_{filter} - fsr_{sensor}|$, the resonances of the filter and sensor resonators will overlap at wavelength $\lambda_1$. The peak of the envelope signal will thus have shifted over a distance $fsr_{filter}$ to larger wavelengths.

The second case is illustrated in the graph in FIG. 15, and occurs when the free spectral range of the filter resonator is smaller than the free spectral range of the sensor resonator. When in this case the resonance wavelengths of the sensor ring resonator shift to larger wavelengths over a spectral distance $|fsr_{filter} - fsr_{sensor}|$, the resonances of the filter and sensor resonators will overlap at wavelength $\lambda_{-1}$. The peak of the envelope signal will thus have shifted over a distance $fsr_{filter}$ to smaller wavelengths.

From both cases, one can conclude that the sensitivity of the sensor consisting of two cascaded ring resonators is equal to the sensitivity of the sensor ring resonator multiplied by a factor $$\frac{fsr_{filter}}{fsr_{filter} - fsr_{sensor}}.$$

This positive is $fsr_{filter} > fsr_{sensor}$ and negative when $fsr_{filter} < fsr_{sensor}$.

When taking first order dispersion into account, the sensitivity of the sensor ring resonator is $$\frac{\partial \lambda_{res}}{\partial n_{enc}} = \frac{\frac{\partial n_{eff,sensor}}{\partial n_{env}} \lambda}{n_{g,sensor}},$$

with $$\frac{\partial \lambda_{res}}{\partial n_{enc}}$$

the sensitivity defined as the change of the resonance wavelength of the sensor ring resonator due to a change of the environment refractive index, $$\frac{\partial n_{eff,sensor}}{\partial n_{env}}$$

the change of the effective index of the sensor ring resonator waveguide due to a change of the refractive index in the environment of the sensor and $n_{g,sensor}$ the group index of the sensor ring resonator waveguide.

The sensitivity of the sensor comprising of two cascaded ring resonators thus is given by:

$$\frac{\partial \lambda_{central}}{\partial n_{env}} = \frac{\partial \lambda_{central}}{\partial \lambda_{res}} \frac{\partial \lambda_{res}}{\partial n_{env}} = \frac{fsr_{filter}}{fsr_{filter} - fsr_{sensor}} \frac{\frac{\partial n_{eff,sensor}}{\partial n_{env}} \lambda}{n_{g,sensor}},$$

with $$\frac{\partial \lambda_{central}}{\partial n_{env}}$$

the sensitivity defined as the change of the central wavelength of the envelope peak due to a change of the refractive index of the environment of the sensor. The sensitivity of the cascaded ring resonator sensor is enhanced with a factor $$\frac{fsr_{filter}}{fsr_{filter} - fsr_{sensor}}$$

compared to the sensitivity of a single ring resonator sensor. In practice the period of the envelope signal of the cascade may not be chosen larger than the available wavelength range of the measurement equipment. For a given envelope period $$\frac{fsr_{sensor} \cdot fsr_{filter}}{|fsr_{sensor} - fsr_{filter}|},$$

the hereinabove obtained expression for the sensitivity is in good approximation proportional to the optical roundtrip length of the resonators in the cascade. Note that for an increasing refractive index $n_{env}$ the resonance wavelength of a single ring resonator will always shift to larger wavelengths, while the central wavelength of the envelope peak in the transmission spectrum of the cascade will shift to smaller wavelengths if $fsr_{filter} < fsr_{sensor}$, and to larger wavelengths if $fsr_{filter} > fsr_{sensor}$.

Figure 7:
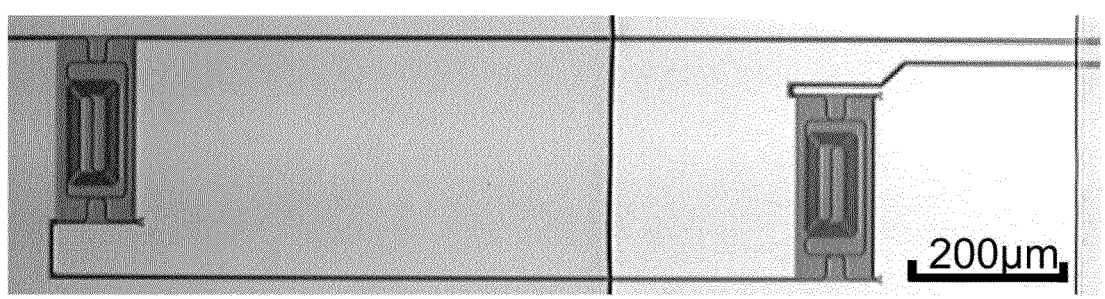
FIG. 7 shows an optical microscopy image of an exemplary sensor fabricated in silicon-on-insulator, as can be used in a method according to an embodiment of the present invention.
Figure 8:
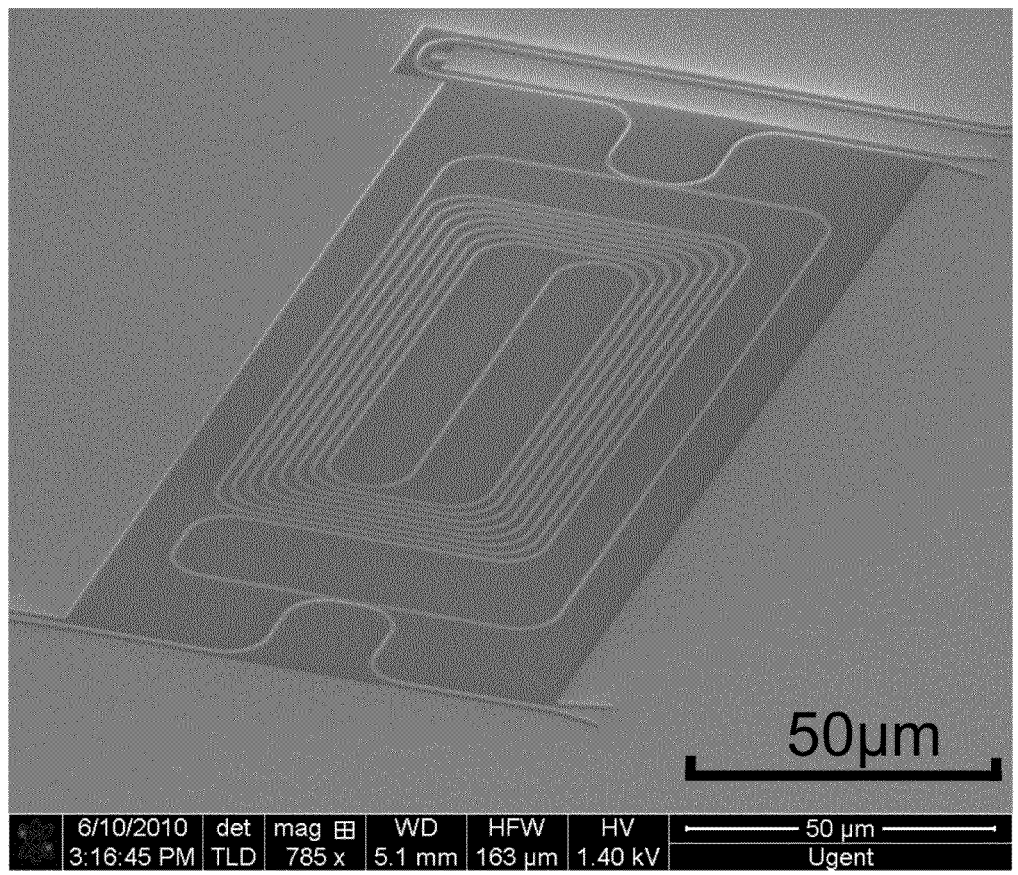
FIG. 8 shows a scanning electron microscopy image of one of the resonators shown in FIG. 7, as can be used in an embodiment of the present invention.

In order to provide an example which illustrates principles of the present invention, a sensor was made in silicon-on-insulator with 2 μm buried oxide and 220 nm silicon top layer with CMOS-compatible 193 nm optical lithography and dry etching. FIG. 7 and FIG. 8 illustrate this device. The device comprises two cascaded ring resonators, further referred to as the filter resonator and the sensor resonator, having a physical roundtrip length of respectively 2528 nm and 2514 nm. By folding the cavity of these resonators, their footprint was reduced to only 200 μm×70 μm. The resonators consist of 450 nm wide single-mode waveguides and each one has two 6 μm long directional couplers with a gap of 180 nm between the waveguides. The complete chip was covered with 500 nm silicon oxide by plasma deposition and a window was etched to the second resonator in the cascade by consecutive dry and wet etching, so that only the evanescent field of this sensor ring resonator can interact with refractive index changes in the environment of the sensor. Note that this example may be suboptimal and only serves as a proof of principle.

To allow controlled delivery of liquids to the sensor, a microfluidic channel with 600 μm×50 μm cross section was made in PDMS by casting and directly bonded to the sensor chip at 135° C. after having applied a short oxygen plasma treatment to both surfaces. The liquids were pumped through the channel over the sensor ring resonator with a syringe pump at a 5 μL/min flow rate. The chip was mounted on a temperature-stabilized chuck to avoid drifting of the sensor signal due to temperature variations. A second-order diffractive grating, integrated on the input and output waveguides, is used to couple from a 10 μm wide ridge waveguide to a vertically oriented, butt-coupled single-mode fiber. The grating has 10 periods of 630 nm with 50 nm etch depth. A linear, 150 μm long taper is employed as a transition between the ridge waveguide and a 450 nm wide photonic wire waveguide. A polarization controller was used to tune the polarization of light from a tunable laser for maximum coupling to the quasi-TE mode of the waveguides, and the optical power transmitted by the sensor was measured with a photodetector.

Figure 9:
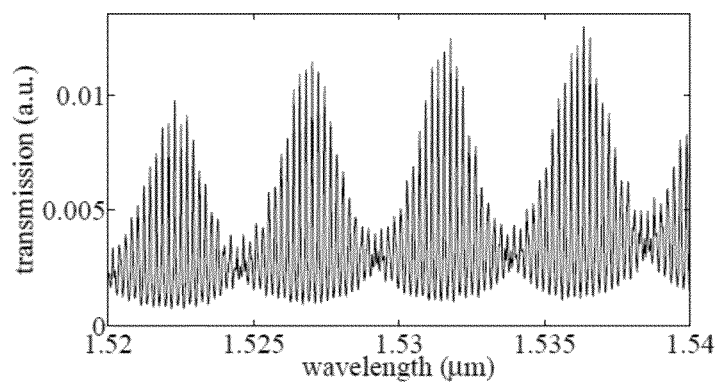
FIG. 9 shows a graph of a measured transmission spectrum of the exemplary device shown in FIG. 7 as de-ionized water is flowing over the sensor ring resonator, as can be used in an embodiment of the present invention.

In FIG. 9, the transmission spectrum of this sensor is plotted, experimentally obtained while deionized water was flowing over the sensor. In accordance with theoretical principles discussed hereinabove, a periodic envelope signal is superposed on the sharp constituent peaks. The height of the envelope peaks varies due to the wavelength-dependent coupling efficiency of the grating couplers.

To obtain a low detection limit, next to having a sensor with a large sensitivity, it is equally important to be able to measure a small shift of the transmission spectrum. This smallest detectable shift is determined by the shape of the spectrum and the noise, but also the method that is adopted to analyze the spectrum has a large impact.

Figure 10:
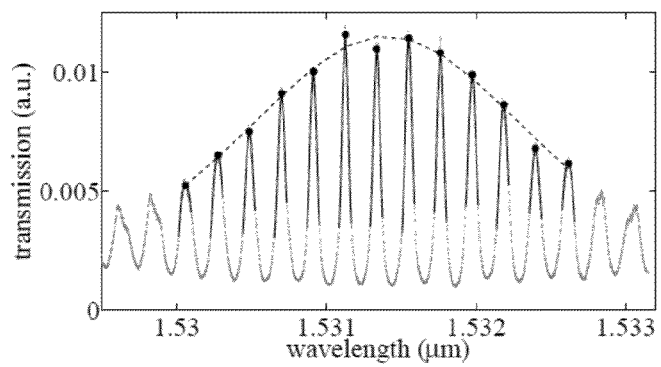
FIG. 10 is an illustration of an exemplary fitting procedure, according to an embodiment of the present invention.

A method according to the first aspect of the present invention may be used to accurately determine the central wavelength of an envelope peak in the transmission spectrum of the cascaded ring resonator sensor, e.g. by fitting the formulas derived in the discussion of theoretical principles hereinabove to the measured spectrum. The fitting procedure is illustrated in FIG. 10.

In a first step, a transmission spectrum, e.g. such as shown in FIG. 9, is measured using the sensor. Then, the formula $$T_{constituent}(\lambda) = \frac{t_{max,filter} \frac{fwhm_{filter}^2}{4}}{\frac{fwhm_{filter}^2}{4} + \left(\lambda - \lambda_0 - \frac{\Delta\lambda}{2}\right)^2} \cdot \frac{t_{max,sensor} \frac{fwhm_{sensor}^2}{4}}{\frac{fwhm_{sensor}^2}{4} + \left(\lambda - \lambda_0 - \frac{\Delta\lambda}{2}\right)^2}$$

is fitted to the measurements. To improve the quality of the fit, only the highest constituent peaks in the transmission spectrum may be used in this fitting procedure, for example, the measurements may be first filtered by discarding data below a predetermined threshold, thus avoiding data with low signal to noise ratio. In FIG. 10, a good correspondence can be observed between the fitted function and the experimental data, which was measured with 1 pm wavelength step. By taking the analytical maximum of the fitted function for each of these constituent peaks, the envelope signal is determined in a noise resistant way.

Then, $$T_{envelope}(\lambda) = \left(\frac{\sqrt{t_{max,filter} \cdot t_{max,sensor}} \left(\frac{FWHM}{2}\right)^2}{\left(\frac{FWHM}{2}\right)^2 + (\lambda - \lambda_{central})^2}\right)^2,$$

with $$FWHM = 2 \cdot \frac{fwhm \cdot \min(fsr_{sensor}, fsr_{filter})}{|fsr_{filter} - fsr_{sensor}|}$$

is fitted to the envelope signal formed by the maxima of each constituent peak fit of the previous step. The position of the analytical maximum of this function, $\lambda_{central}$, is taken as the central wavelength of the measured envelope peak.

A good measure for the smallest detectable wavelength shift with this method is given by the standard deviation on the fitted central wavelength of the envelope peak. Based on the confidence interval of the fitting parameters returned by our standard fitting software, the smallest detectable wavelength shift was calculated to be 18 pm for the measured spectra of our sensor. Note that this value is an order of magnitude smaller than the distance between the peaks in the spectrum.

Figure 11:
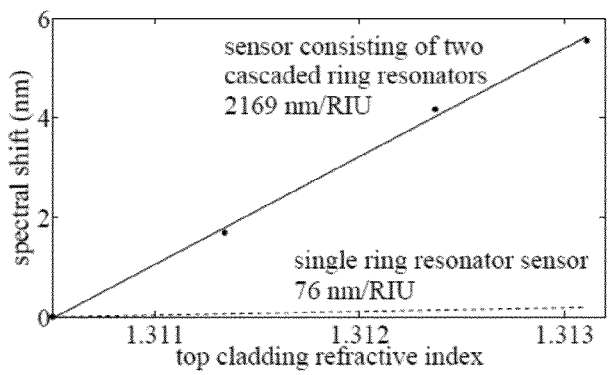
FIG. 11 shows shift of the transmission spectrum of the sensor as a function of the bulk refractive index in its top cladding, as can be used in an embodiment according to the present invention.

To measure the sensitivity of the sensor to changes in the bulk refractive index of its aqueous environment, it was measured how much the envelope peaks in the transmission spectrum shifted when changing between flowing deionised water and three aqueous solutions of NaCl having different concentrations. The refractive index of each of these solutions was calculated. In FIG. 11 the dots indicate the measured shifts as a function of bulk refractive index. A linear function was fitted to the measured shifts, and its slope revealed a sensitivity of 2169 nm/RIU. This value corresponds well with the theoretical sensitivity of 2085 nm/RIU calculated with $$\frac{\partial \lambda_{central}}{\partial n_{env}} = \frac{fsr_{filter}}{fsr_{filter} - fsr_{sensor}} \frac{\frac{\partial n_{eff,sensor}}{\partial n_{env}} \lambda}{n_{g,sensor}}.$$

The large sensitivity of this sensor, combined with a data-analysis method according to the present invention, makes it very well suited for integration with on-chip dispersive elements such as arrayed waveguide gratings or planar concave gratings, giving opportunities for cheaper and more portable sensor read-out.

For comparison, the resonance wavelength shift of a single ring resonator comprised of a 450 nm wide waveguide is calculated to be 76 nm/RIU, showing the large sensitivity improvement with the presented method and a double ring resonator sensor.

The resulting detection limit of the sensor is equal to the ratio of the smallest detectable wavelength shift and the sensitivity, that is 18 pm/(2169 nm/RIU)=8.3 $10^{-6}$ RIU. It should be noted in this respect that the spectral measurements for this example were obtained with a sensor which was not optimized in design to achieve an optimal or near-optimal detection limit. Such optimizations may be carried out by a skilled person using common background knowledge in the art. The detection limit obtained for this exemplary sensor is however comparable to that for a state-of-the-art single ring resonator sensor.

The invention claimed is:

1. A method for quantifying an effective refractive index change in a photonic sensor the method comprising the steps of:
    obtaining spectral data representative for an optical signal being modulated with an optical transfer characteristics of the photonic sensor, the modulation being obtained by combining modulation of a first electromagnetic wave component in a optical filter element with a first periodic transfer spectrum having a first free spectral range and modulation of a second electromagnetic wave component in an optical filter element with a second periodic transfer spectrum having a second free spectral range being different from the first free spectral range, wherein a relative change is induced in the second periodic transfer spectrum with respect to the first periodic transfer spectrum as a result of changing environmental conditions or conformational changes of the photonic sensor, and
    quantifying the effective refractive index change of the photonic sensor taking into account said spectral data,
    wherein said quantifying comprises determining a wavelength offset of an envelope signal applied to the spectral data, the envelope signal having a wavelength periodicity substantially larger than a periodicity of the first periodic transfer spectrum and the second periodic transfer spectrum.

2. A method according to claim 1, wherein said first periodic transfer spectrum and/or said second periodic transfer spectrum is a comb filter.

3. A method according to claim 1, in which said determining a wavelength offset of an envelope signal comprises determining a plurality of wavelength locations corresponding to a plurality of peaks and/or valleys in said spectral data.

4. A method according to claim 3, wherein determining a plurality of wavelength locations corresponding to a plurality of peaks and/or valleys comprises:
    identifying a plurality of intermittent peaks and/or valleys in said spectral data, and,
    for each pair of successive peaks and/or valleys, fitting a first function having a first wavelength location parameter to the spectral data obtained for wavelengths in the range defined by said pair of successive peaks and/or valleys, in order to obtain a plurality of first wavelength location parameter values and amplitude values.

5. A method according to claim 4, wherein said plurality of peaks and/or valleys are selected such that the spectral data value corresponding to the peak wavelength exceeds a predetermined threshold value.

6. A method according to claim 4, wherein said first function comprises a product of Lorentzian functions.

7. A method according to claim 3, wherein said determining a wavelength offset of an envelope signal further comprises fitting a second function having a second wavelength location parameter to said plurality of first wavelength locations parameter values and amplitude values.

8. A method according to claim 7, wherein said second function comprises a square of a Lorentzian function.

9. A method according to claim 7, wherein said fitting a second function comprises a non-linear regression technique.

10. A method according to claim 1, wherein the difference between the first free spectral range and the second free spectral range is smaller than or equal to a largest full width at half maximum of the peaks in the first and second periodic transfer spectrum.

11. A method according to claim 1, wherein the second electromagnetic wave component is the modulated first electromagnetic wave component.

12. A method according to claim 1, wherein obtaining the spectral data comprises
    coupling a first electromagnetic wave into at least one optical filter implemented on a photonic sensor,
    applying a modulation with a first periodic transfer spectrum to said first electromagnetic wave component using said at least one optical filter element,
    applying a modulation with a second periodic transfer spectrum to said second electromagnetic wave component using at least one optical filter element, the first and second periodic transfer spectrum having a different free spectral range,
    contacting said photonic sensor to a test medium such that the refractive index of the test medium influences a relative wavelength shift in the first periodic transfer spectrum with respect to the second periodic transfer spectrum.

13. A method according to claim 12, wherein for said obtaining spectral data, the method further comprises providing a photonic sensor, the photonic sensor comprising:
    an input waveguide structure for receiving a first electromagnetic wave, at least one optical filter element coupled to said input waveguide structure and configured for causing optical interference so as to apply said first modulating with said first periodic transfer spectrum and said second modulating with said second periodic transfer spectrum, and an output waveguide structure for coupling a combination of said first electromagnetic wave, modulated by the first periodic transfer spectrum, and said second electromagnetic wave, modulated by the second periodic transfer spectrum, out of the photonic sensor.

14. A method according to claim 13, wherein said photonic sensor comprises a first optical filter element being optically coupled in sequence to a second optical filter element, the first and second optical filter element being arranged such that the refractive index of said test medium influences a wavelength shift of the transmission spectrum of at least one of the first and second optical filter element, and the first optical filter element and second optical filter element have free spectral ranges differing such that a Vernier configuration is achieved.

15. A method according to claim 1, wherein the first optical filter element and/or the second optical filter element is any of a resonator and/or an interferometer.

16. A method according to claim 1, wherein the combining comprises a multiplication.

17. A method according to claim 1, wherein said obtaining spectral data comprises obtaining data for a plurality of measurements of intensity, transmittance and/or absorbance.

18. A non-transitory computer program product for, when executing on a processing unit, quantifying an effective refractive index change in a photonic sensor by:
obtaining spectral data representative for an optical signal being modulated with an optical transfer characteristics of the photonic sensor, the modulation being obtained by combining modulation of a first electromagnetic wave component in an optical filter element with a first periodic transfer spectrum having a first free spectral range and modulation of a second electromagnetic wave component in an optical filter element with a second periodic transfer spectrum having a second free spectral range being different from the first free spectral range, wherein a relative change is induced in the second periodic transfer spectrum with respect to the first periodic transfer spectrum as a result of changing environmental conditions or conformational changes of the photonic sensor, and
quantifying the effective refractive index change of the photonic sensor taking into account said spectral data,
wherein said quantifying comprises determining a wavelength offset of an envelope signal applied to the spectral data, the envelope signal having a wavelength periodicity substantially larger than a periodicity of the first periodic transfer spectrum and the second periodic transfer spectrum.

19. A processor for quantifying an effective refractive index change in a photonic sensor, the processor being programmed for determining a wavelength offset of an envelope signal in spectral data, the envelope signal having a wavelength periodicity substantially larger than a periodicity of the first periodic transfer spectrum and the second periodic transfer spectrum,
wherein said spectral data are representative for an optical signal being modulated with an optical transfer characteristics of a photonic sensor, the modulation being obtained by combining modulation of a first electromagnetic wave component in an optical filter element with a first periodic transfer spectrum having a first free spectral range and modulation of a second electromagnetic wave component in an optical filter element with a second periodic transfer spectrum having a second free spectral range being different from the first free spectral range, wherein a relative change is induced in the second periodic transfer spectrum with respect to the first periodic transfer spectrum as a result of changing environmental conditions or conformational changes of the photonic sensor.

20. A system comprising:
a processor according to claim 19, the processor being embedded in a system, and
a sensor comprising an input waveguide structure for receiving a first electromagnetic wave, at least one optical filter element coupled to said input waveguide structure and configured for causing optical interference so as to apply said first modulating with said first periodic transfer spectrum and said second modulating with said second periodic transfer spectrum, and an output waveguide structure for coupling a combination of said first electromagnetic wave, modulated by the first periodic transfer spectrum, and said second electromagnetic wave, modulated by the second periodic transfer spectrum, out of the photonic sensor, a light source for coupling a first electromagnetic wave into said at least one optical filter element and a detector for determining the spectral data.

* * * * *